(12) United States Patent
Gisselberg et al.

(10) Patent No.: US 8,196,589 B2
(45) Date of Patent: *Jun. 12, 2012

(54) IMPLANTABLE MARKER WITH WIRELESS SIGNAL TRANSMITTER

(75) Inventors: Margo Gisselberg, Lynnwood, WA (US); Keith Seiler, Issaquah, WA (US); Steven C. Dimmer, Bellevue, WA (US)

(73) Assignee: Calypso Medical Technologies, Inc., Seattle, WA (US)

(*) Notice: Subject to any disclaimer, the term of this patent is extended or adjusted under 35 U.S.C. 154(b) by 2086 days.

This patent is subject to a terminal disclaimer.

(21) Appl. No.: 10/746,888

(22) Filed: Dec. 24, 2003

(65) Prior Publication Data

US 2005/0154293 A1 Jul. 14, 2005

(51) Int. Cl.
*A61B 19/00* (2006.01)

(52) U.S. Cl. .......... 128/899; 600/424; 600/431

(58) Field of Classification Search ........ 600/424, 600/431; 128/899
See application file for complete search history.

(56) References Cited

U.S. PATENT DOCUMENTS

| | | |
|---|---|---|
| 3,752,960 A | 8/1973 | Walton |
| 3,836,842 A | 9/1974 | Zimmermann et al. |
| 3,967,161 A | 6/1976 | Lichtblau |
| 4,017,858 A | 4/1977 | Kuipers |
| 4,023,167 A | 5/1977 | Wahlstrom |
| 4,065,753 A | 12/1977 | Paul, Jr. |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson |
| 4,230,123 A | 10/1980 | Hawkins |
| 4,260,990 A | 4/1981 | Lichtblau |
| 4,393,872 A | 7/1983 | Reznik |
| 4,395,910 A | 8/1983 | Thomenius |
| 4,466,075 A | 8/1984 | Groch |
| 4,618,978 A | 10/1986 | Cosman |
| 4,633,250 A | 12/1986 | Anderson |
| 4,642,786 A | 2/1987 | Hansen |
| 4,643,196 A | 2/1987 | Tanaka |
| 4,737,794 A | 4/1988 | Jones |
| 4,795,995 A | 1/1989 | Eccleston |

(Continued)

FOREIGN PATENT DOCUMENTS

EP 0719420 7/1996

(Continued)

OTHER PUBLICATIONS

U.S. Appl. No. 10/416,827, filed Nov. 17, 2000, David Krag.

(Continued)

*Primary Examiner* — Long V Le
*Assistant Examiner* — Ellsworth Weatherby
(74) *Attorney, Agent, or Firm* — Perkins Coie LLP

(57) ABSTRACT

A wireless marker for localizing a target of a patient comprises a casing and a magnetic transponder at least partially received in the casing. The magnetic transponder produces a wirelessly transmitted magnetic field in response to a wirelessly transmitted excitation energy. The magnetic transponder also has a magnetic centroid. The marker also comprises an imaging element carried by the casing and/or the magnetic transponder. The imaging element has a radiographic profile in a radiographic image such that the marker has a radiographic centroid at least approximately coincident with the magnetic centroid.

37 Claims, 5 Drawing Sheets

U.S. PATENT DOCUMENTS

| | | | |
|---|---|---|---|
| 4,799,495 A | 1/1989 | Hawkins | |
| 4,832,055 A | 5/1989 | Palestrant | |
| 4,849,692 A | 7/1989 | Blood | |
| 4,909,789 A | 3/1990 | Taguchi | |
| 4,936,823 A | 6/1990 | Colvin | |
| 4,945,305 A | 7/1990 | Blood | |
| 4,989,608 A * | 2/1991 | Ratner | 600/420 |
| 4,992,794 A | 2/1991 | Brouwers | |
| 4,994,079 A | 2/1991 | Genese | |
| 5,031,634 A | 7/1991 | Simon | |
| 5,050,608 A | 9/1991 | Watanabe | |
| 5,062,847 A | 11/1991 | Barnes | |
| 5,095,224 A | 3/1992 | Renger | |
| 5,099,845 A | 3/1992 | Besz | |
| 5,107,862 A | 4/1992 | Fabian | |
| 5,142,292 A | 8/1992 | Chang | |
| 5,170,055 A | 12/1992 | Carroll | |
| 5,188,368 A | 2/1993 | Ryan | |
| 5,197,466 A | 3/1993 | Marchosky | |
| 5,198,877 A | 3/1993 | Schulz | |
| 5,205,289 A | 4/1993 | Hardy | |
| 5,211,129 A | 5/1993 | Taylor | |
| 5,211,164 A | 5/1993 | Allen | |
| 5,221,269 A | 6/1993 | Miller | |
| 5,223,851 A | 6/1993 | Hadden | |
| 5,230,338 A | 7/1993 | Allen | |
| 5,240,011 A | 8/1993 | Assa | |
| 5,246,005 A | 9/1993 | Carroll | |
| 5,262,772 A | 11/1993 | Urbas | |
| 5,325,873 A | 7/1994 | Hirschi | |
| 5,377,678 A | 1/1995 | Dumoulin | |
| 5,397,329 A | 3/1995 | Allen | |
| 5,411,026 A | 5/1995 | Carol | |
| 5,417,210 A | 5/1995 | Funda | |
| 5,425,367 A | 6/1995 | Shapiro | |
| 5,425,382 A | 6/1995 | Golden | |
| 5,446,548 A | 8/1995 | Gerig | |
| 5,453,686 A | 9/1995 | Anderson | |
| 5,509,900 A | 4/1996 | Kirkman | |
| 5,515,853 A | 5/1996 | Smith | |
| 5,526,812 A | 6/1996 | Dumoulin | |
| 5,528,651 A | 6/1996 | Leksell | |
| 5,546,951 A | 8/1996 | Ben-Haim | |
| 5,558,091 A | 9/1996 | Acker | |
| 5,568,809 A | 10/1996 | Ben-Haim | |
| 5,572,999 A | 11/1996 | Funda | |
| 5,617,857 A | 4/1997 | Chader | |
| 5,622,170 A | 4/1997 | Schulz | |
| 5,622,187 A | 4/1997 | Carol | |
| 5,629,967 A | 5/1997 | Leksell | |
| 5,630,431 A | 5/1997 | Taylor | |
| 5,645,065 A | 7/1997 | Shapiro | |
| 5,680,106 A | 10/1997 | Schrott | |
| 5,681,326 A | 10/1997 | Lax | |
| 5,697,384 A | 12/1997 | Miyawaki | |
| 5,707,362 A | 1/1998 | Yoon | |
| 5,707,390 A | 1/1998 | Bonutti | |
| 5,727,552 A | 3/1998 | Ryan | |
| 5,745,545 A | 4/1998 | Hughes | |
| RE35,816 E | 6/1998 | Schulz | |
| 5,764,052 A | 6/1998 | Renger | |
| 5,769,861 A | 6/1998 | Vilsmeier | |
| 5,779,638 A | 7/1998 | Vesely | |
| 5,782,775 A | 7/1998 | Milliman | |
| 5,797,849 A | 8/1998 | Vesely | |
| 5,805,661 A | 9/1998 | Leksell | |
| 5,815,076 A | 9/1998 | Herring | |
| 5,817,022 A | 10/1998 | Vesely | |
| 5,817,092 A | 10/1998 | Behl | |
| 5,820,553 A | 10/1998 | Hughes | |
| 5,823,192 A | 10/1998 | Kalend | |
| 5,828,770 A | 10/1998 | Leis | |
| 5,830,144 A | 11/1998 | Vesely | |
| 5,840,148 A | 11/1998 | Campbell | |
| 5,868,673 A | 2/1999 | Vesely | |
| 5,868,675 A | 2/1999 | Henrion | |
| 5,879,297 A | 3/1999 | Haynor | |
| 5,879,357 A | 3/1999 | Heaton | |
| 5,895,235 A | 4/1999 | Droz | |
| 5,902,238 A | 5/1999 | Golden | |
| 5,902,310 A | 5/1999 | Foerster | |
| 5,907,395 A | 5/1999 | Schulz | |
| 5,910,144 A | 6/1999 | Hayashi | |
| 5,913,820 A | 6/1999 | Bladen | |
| 5,923,417 A | 7/1999 | Leis | |
| 5,951,481 A | 9/1999 | Evans | |
| 5,963,132 A | 10/1999 | Yoakum | |
| 5,987,349 A | 11/1999 | Schulz | |
| 5,989,265 A | 11/1999 | Bouquet De La Joliniere | |
| 6,015,390 A | 1/2000 | Krag | |
| 6,019,725 A | 2/2000 | Vesely | |
| 6,026,818 A * | 2/2000 | Blair et al. | 128/899 |
| 6,049,587 A | 4/2000 | Leksell | |
| 6,052,477 A | 4/2000 | Wang | |
| 6,059,734 A | 5/2000 | Yoon | |
| 6,061,644 A | 5/2000 | Leis | |
| 6,064,904 A | 5/2000 | Yanof | |
| 6,067,465 A | 5/2000 | Foo | |
| 6,076,008 A | 6/2000 | Bucholz | |
| 6,082,366 A | 7/2000 | Andra | |
| 6,094,007 A | 7/2000 | Faul | |
| 6,097,007 A | 8/2000 | Wang | |
| 6,097,994 A | 8/2000 | Navab | |
| 6,129,658 A | 10/2000 | Delfino | |
| 6,130,612 A | 10/2000 | Castellano | |
| 6,140,740 A | 10/2000 | Porat | |
| 6,144,875 A | 11/2000 | Schweikard | |
| 6,173,715 B1 | 1/2001 | Sinanan | |
| 6,198,963 B1 | 3/2001 | Ben Haim | |
| 6,239,724 B1 | 5/2001 | Doron | |
| 6,272,370 B1 * | 8/2001 | Gillies et al. | 600/411 |
| 6,363,940 B1 | 4/2002 | Krag | |
| 6,363,982 B1 | 4/2002 | Nixon, Jr. | |
| 6,371,379 B1 | 4/2002 | Dames | |
| 6,385,482 B1 | 5/2002 | Boksberger | |
| 6,400,338 B1 | 6/2002 | Mejia | |
| 6,401,722 B1 | 6/2002 | Krag | |
| 6,419,680 B1 * | 7/2002 | Cosman et al. | 606/130 |
| 6,441,741 B1 * | 8/2002 | Yoakum | 340/572.8 |
| 6,474,341 B1 | 11/2002 | Hunter | |
| 6,518,884 B1 | 2/2003 | Tanji | |
| 6,529,760 B2 * | 3/2003 | Pantages et al. | 600/407 |
| 6,675,810 B2 | 1/2004 | Krag | |
| 6,698,433 B2 | 3/2004 | Krag | |
| 6,734,795 B2 | 5/2004 | Price | |
| 6,812,842 B2 | 11/2004 | Dimmer | |
| 2001/0004395 A1 * | 6/2001 | McCrory et al. | 378/162 |
| 2001/0018594 A1 | 8/2001 | Krag | |
| 2002/0193685 A1 * | 12/2002 | Mate et al. | 600/424 |
| 2003/0052785 A1 | 3/2003 | Gisselberg | |
| 2003/0066537 A1 * | 4/2003 | Fabian et al. | 128/899 |
| 2003/0088178 A1 | 5/2003 | Owens et al. | |
| 2003/0117269 A1 | 6/2003 | Dimmer | |
| 2003/0117270 A1 | 6/2003 | Dimmer | |
| 2003/0120146 A1 * | 6/2003 | Dumoulin | 600/410 |
| 2003/0192557 A1 | 10/2003 | Krag | |
| 2004/0074974 A1 | 4/2004 | Senba | |
| 2004/0127787 A1 | 7/2004 | Dimmer | |
| 2007/0161884 A1 * | 7/2007 | Black et al. | 600/407 |

FOREIGN PATENT DOCUMENTS

| | | |
|---|---|---|
| EP | 1034738 | 9/2000 |
| FR | 26335259 | 2/1990 |
| WO | WO-88/08282 | 11/1988 |
| WO | WO-95/33519 | 12/1995 |
| WO | WO-96/08208 | 3/1996 |
| WO | WO-96/08999 | 3/1996 |
| WO | WO-97/36192 | 10/1997 |
| WO | WO-97/48438 | 12/1997 |
| WO | WO-98/30166 | 7/1998 |
| WO | WO-99/13775 | 3/1999 |
| WO | WO-99/17133 | 4/1999 |
| WO | WO-99/27839 | 6/1999 |
| WO | WO-99/30182 | 6/1999 |
| WO | WO-99/35966 | 7/1999 |
| WO | WO-99/44506 | 9/1999 |
| WO | WO-99/58055 | 11/1999 |

| | | |
|---|---|---|
| WO | WO-99/58065 | 11/1999 |
| WO | WO-00/12009 | 3/2000 |
| WO | WO-00/24332 | 5/2000 |
| WO | WO-00/51514 | 9/2000 |
| WO | WO-00/71047 | 11/2000 |
| WO | WO-01/34049 | 5/2001 |
| WO | WO-01/54765 | 8/2001 |
| WO | WO-02/19908 | 3/2002 |
| WO | WO-02/100485 | 12/2002 |

OTHER PUBLICATIONS

U.S. Appl. No. 10/745,097, filed Dec. 23, 2003, Steven C. Dimmer.
U.S. Appl. No. 10/745,104, filed Dec. 23, 2003, David Krag.
U.S. Appl. No. 10/791,662, filed Mar. 2, 2004, David Krag.
International Search Report dated Jul. 16, 1999, PCT Application No. PCT/US99/10683.
PCT Written Opinion dated Jul. 8, 2003, PCT Application No. PCT/US00/31667.
International Search Report dated Jan. 24, 2003, PCT Application No. PCT/US02/29390.
The World's Most Versatile Biopsy System Offered Only by USSC, ABBI* System Features, © 1997, United States Surgical Corporation, www.ussurg.com/health-care/procedures/abbi.
Kelley, William E., MD, Image-Guided Breast Biopsy: The ABBI* System, 1997, www.ussurg.com/health-care/procedures/abbi.
International Search Report dated Jul. 3, 2001, PCT Application No. PCT/US00/31667.
Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.
International Search Report dated Oct. 8, 2002, PCT Application No. PCT/US02/17876.
International Search Report dated Apr. 13, 2001, PCT Application No. PCT/US00/31673.

* cited by examiner

IMPLANTABLE MARKER WITH WIRELESS SIGNAL TRANSMITTER

TECHNICAL FIELD

The present invention is directed toward markers with signal transmitters that wirelessly transmit location signals and are suitable for use in radiation imaging processes. Several embodiments of the markers are permanently implantable or semi-permanently implantable in patients for locating at least one target in and/or on the patient.

BACKGROUND

Medical procedures often require locating and treating target areas within a patient. Radiation therapy and many surgical procedures require locating the target with a high degree of precision to limit collateral damage to healthy tissue around the target. It is particularly important to know or estimate the precise location of the target in radiation oncology because it is (a) desirable to accurately determine the accumulated dosage applied to the target and (b) detrimental to expose adjacent body parts to the radiation. In applications for treating prostate cancer, for example, it is detrimental to irradiate the colon, bladder or other neighboring body parts with the high-intensity radiation beam. Surgical applications, such as breast surgery and other procedures involving soft tissue, also require knowing the precise location of a target because a lesion in soft tissue is not necessarily fixed relative to external landmarks on the patient.

Many imaging systems have been used to locate areas or particular targets in a patient before performing radiation oncology or surgical procedures. Although x-ray, Magnetic Resonance Imaging (MRI), CT and other imaging techniques are useful to locate targets within the body at a pre-operative stage of a procedure, they are often not suitable or difficult to use in real time during surgery or radiation therapy. For example, the location of a lesion in soft tissue or in an organ may shift relative to external landmarks on the patient between the pre-operative imaging procedure and the actual radiation or surgical procedure. Additionally, when imaging systems are used during a radiation or surgical procedure, they may not provide sufficiently accurate measurements of the location of the lesions and they may interfere with the radiation or surgical procedure. Therefore, imaging techniques by themselves are generally not well suited for accurately identifying the actual location of a target for many medical applications.

Another technique to locate a target in a patient is to implant a marker relative to the target. Several types of tags or markers with resonating magnetic circuits have been developed to track feeding tubes, tag items, and mark tissue. For example, implantable markers that generate a signal have been proposed for use to locate a selected target in a patient in radiation oncology procedures. U.S. Pat. No. 6,385,482 B1 issued to Boksberger et al. discloses a device having an implanted emitter unit located inside or as close as possible to a target object, and a plurality of receiver units that are located outside of the patient. Boksberger discloses determining the location of the target object by energizing the emitter unit using a generator and sensing the signal from the emitter unit with the receiver units. Boksberger discloses and claims that the receiver units are configured to determine the gradient of the magnetic field generated by the emitter unit. Boksberger further discloses that the emitter unit is energized using a wired connection to the external generator. Boksberger also indicates that it is conceivable to use an emitter unit that is energized by a battery or excited by an electromagnetic field generated by the external generator. The wired device disclosed in Boksberger, however, may not be suitable for use in radiation oncology and many surgical procedures because it is impractical to leave a wired marker implanted in a patient for the period of time of such procedures (e.g., five to forty days). Moreover, Boksberger does not disclose or suggest anything with respect to providing an implantable emitter unit that is (a) suitable for use in radiation imaging processes or (b) compatible for use in magnetic resonance imaging devices after being implanted in a patient.

One challenge of using markers with resonating magnetic circuits is determining the relative location between the marker and the target so that the target can be tracked during a procedure or therapy. Accurately determining the location of the marker relative to the target is a precondition for accurately tracking the target based on the resonating magnetic field generated by the implanted marker. One reason that it is difficult to accurately determine the location of the marker relative to the target is that it can be difficult to identify magnetic resonating markers in radiographic images. The markers are difficult to see in radiographic images because (a) they should be very small so that they may be implanted for an extended period of time, and (b) they may not be sufficiently visible in high voltage radiation applications (i.e., megavolt radiation imaging). Moreover, even when a magnetic marker can be identified in an image, it can still be challenging to determine the orientation of the magnetic field generated by the marker relative to the target because it is often difficult to determine the orientation of the marker in the image. As such, implantable markers with resonating magnetic circuits may be difficult to use in radiation therapies and surgical procedures that require highly accurate localization of the target.

DETAILED DESCRIPTION

A. Overview

Figure 1A:
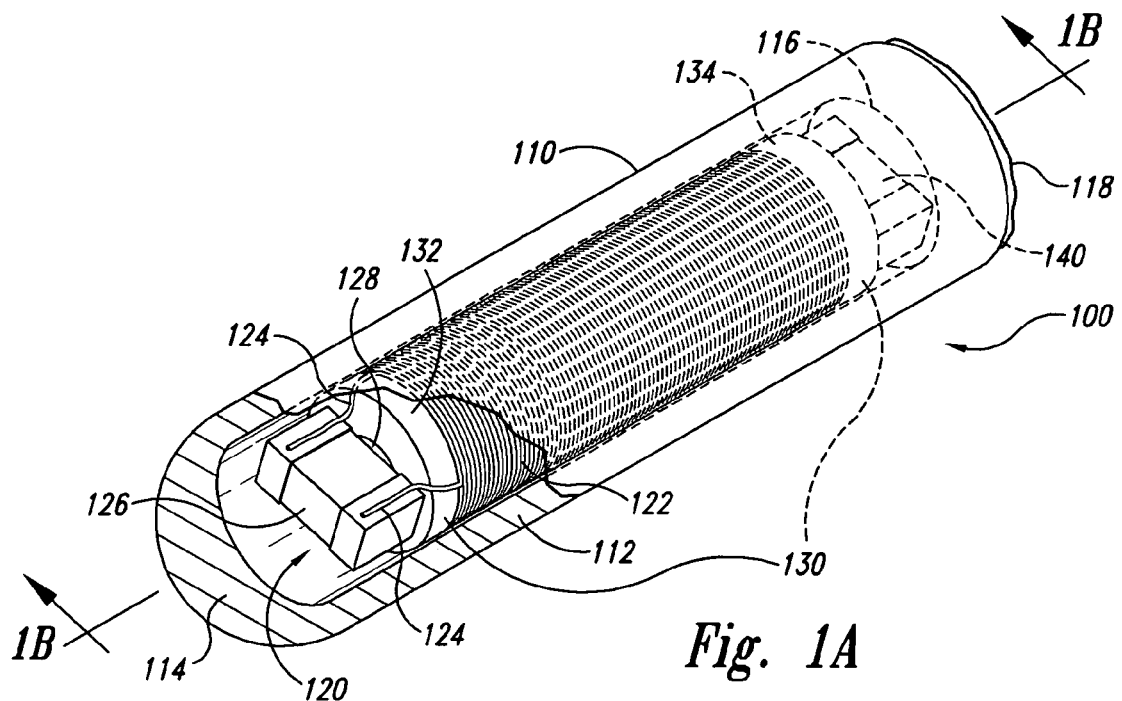
FIG. 1A is an isometric view of a wireless marker in accordance with an embodiment of the invention with a section cut away to illustrate internal components.

The following disclosure describes several embodiments of wireless markers configured to be attached to a patient either by being implanted into the patient or adhered externally to the skin of the patient. The markers are highly suitable for use in radiographic imaging systems and other types of imaging systems to determine the location and orientation of the magnetic field with respect to the target of the patient. Several embodiments of the marker are also compatible for use in powerful magnetic fields generated by magnetic resonance imaging devices. Several embodiments and features of markers in accordance with the invention are set forth and described in FIGS. 1-5, but other embodiments of markers in accordance with the invention can include additional or different features than those shown in FIGS. 1-5. Additionally, several embodiments of the markers in accordance with the invention do not include all the features shown in these Figures. For the purposes of brevity, like reference numbers refer to similar or identical components of the markers in FIGS. 1-5.

One embodiment of a wireless marker for localizing a target of a patient comprises a casing and a magnetic transponder at least partially received in the casing. The magnetic transponder produces a wirelessly transmitted magnetic field in response to a wirelessly transmitted excitation energy. The magnetic transponder also has a magnetic centroid. The marker also comprises an imaging element carried by the casing and/or the magnetic transponder. The imaging element has a radiographic profile in a radiographic image such that the marker has a radiographic centroid at least approximately coincident with the magnetic centroid.

The imaging element can have several different configurations and be composed of many different materials. For example, to be visible on megavoltage x-ray images, the imaging element can comprise a single contrast element or a plurality of contrast elements composed of a high density material and having a sufficient thickness and cross-sectional area to absorb a substantial fraction of photons incident on the imaging element. The image is formed by the reduction of photon flux density in the path from the x-ray source through the imaging element to a radiographic imaging device or film. In other applications that use lower acceleration voltages for the imaging radiation, the imaging element can be a contrast element having a lower density or a different configuration that is not suitable for use with megavoltage x-ray images.

In one embodiment the imaging element comprises first and second contrast elements configured symmetrically with respect to the magnetic transponder. The first and second contrast elements can comprise first and second rings positioned symmetrically with respect to the radiographic and magnetic centroids. The first and second rings can be continuous rings or discontinuous members having a gap. The first and second contrast elements can alternatively be spheres, cubes, or other suitable shapes for identifying the profile of the marker in a radiographic image.

Another embodiment of a wireless marker for localizing a target of a patient in accordance with the invention comprises a casing and a magnetic transponder in the casing. The magnetic transponder produces a wirelessly transmitted magnetic field in response to a wirelessly transmitted excitation field, and it has a first density. The marker of this embodiment further comprises an imaging element carried by the casing and/or the magnetic transponder. The imaging element has a second density greater than the first density of the magnetic transponder.

In yet another embodiment of the invention, a wireless marker for localizing a target of a patient comprises a casing and a magnetic transponder that produces a wirelessly transmitted magnetic field in response to a wirelessly transmitted excitation field. The marker further comprises an imaging element (e.g., a contrast element) carried by the casing and/or the magnetic transponder. In this embodiment, the imaging element is sufficiently absorbent of incident photon fluence of a megavolt photon therapy beam to be visible in a radiographic image generated using such a therapy beam.

Another embodiment of the wireless marker for localizing a target in a patient comprises a casing and a magnetic transponder that produces a wirelessly transmitted magnetic field in response to a wirelessly transmitted excitation field. The marker of this embodiment further comprises an imaging element carried by the casing and/or the magnetic transponder. The imaging element of this embodiment has a density of at least 19 g/cm$^3$.

The invention further includes methods for tracking a target of a patient. For example, one embodiment of such a method comprises imaging a marker attached to the patient using a first energy to obtain an image of the marker. The marker has a magnetic transponder that produces a wirelessly transmitted signal in response to a wirelessly transmitted excitation energy. The method further includes locating the marker by transmitting the excitation energy to the marker.

B. Embodiments of Markers

FIG. 1A is an isometric view of a marker 100 in accordance with an embodiment of the invention with a portion cut away to illustrate internal components. The embodiment of the marker 100 shown in FIG. 1 includes a casing 110 and a magnetic transponder 120 (e.g., a resonating circuit) in the casing 110. The casing 110 is a biocompatible barrier configured to be implanted in the patient, adhered externally to the skin of the patient, or otherwise attached to the patient. The casing 110 can be a generally cylindrical capsule that is sized to fit within a needle for percutaneous implantation, but the casing 110 can have other configurations and be larger or smaller. The casing 110, for example, can have barbs or other features to anchor the casing 110 in soft tissue or an adhesive for attaching the casing 110 externally to the skin of a patient. Suitable anchoring mechanisms for securing the marker 100 to a patient are disclosed in International Publication No. WO 02/39917 A1, which designates the United States and is incorporated herein by reference. In one embodiment, the casing 110 includes (a) a capsule or shell 112 having a closed end 114 and an open end 116, and (b) a sealant 118 in the open end 116 of the shell 112. The casing 110 and the sealant 118 can be made from plastics, ceramics, glass or other suitable biocompatible materials.

The magnetic transponder 120 can include a resonating circuit that produces a wirelessly transmitted signal in response to a wirelessly transmitted excitation field. In one embodiment, the magnetic transponder 120 comprises a coil 122 defined by a plurality of windings of a conductor 124. Many embodiments of the magnetic transponder 120 also include a capacitor 126 coupled to the coil 122. The coil 122 resonates at a selected resonate frequency. The coil 122 can resonate at a resonate frequency solely using the parasitic capacitance of the windings without having a capacitor, or the resonate frequency can be produced using the combination of the coil 122 and the capacitor 126. The coil 122 accordingly defines a signal transmitter that generates an alternating magnetic field at the selected resonate frequency in response to the excitation energy either by itself or in combination with the capacitor 126. The conductor 124 of the illustrated embodiment can be hot air or alcohol bonded wire having a gauge of approximately 45-52. The coil 122 can have 800-1000 turns, and the windings are preferably wound in a tightly layered coil. The magnetic transponder 120 can further include a core 128 composed of a material having a suitable magnetic permeability. For example, the core 128 can be a ferromagnetic element composed of ferrite or another material. Suitable embodiments of magnetic transponders are disclosed in U.S.

patent application Ser. No. 10/334,698. The magnetic transponder 120 can be secured to the casing 110 by an adhesive 129.

The marker 100 also includes an imaging element that enhances the radiographic image of the marker to make the marker more discernible in radiographic images. The imaging element also has a radiographic profile in a radiographic image such that the marker has a radiographic centroid at least approximately coincident with the magnetic centroid of the magnetic transponder 120. As explained in more detail below, the radiographic and magnetic centroids do not need to be exactly coincident with each other, but rather can be within an acceptable range.

Figure 1B:
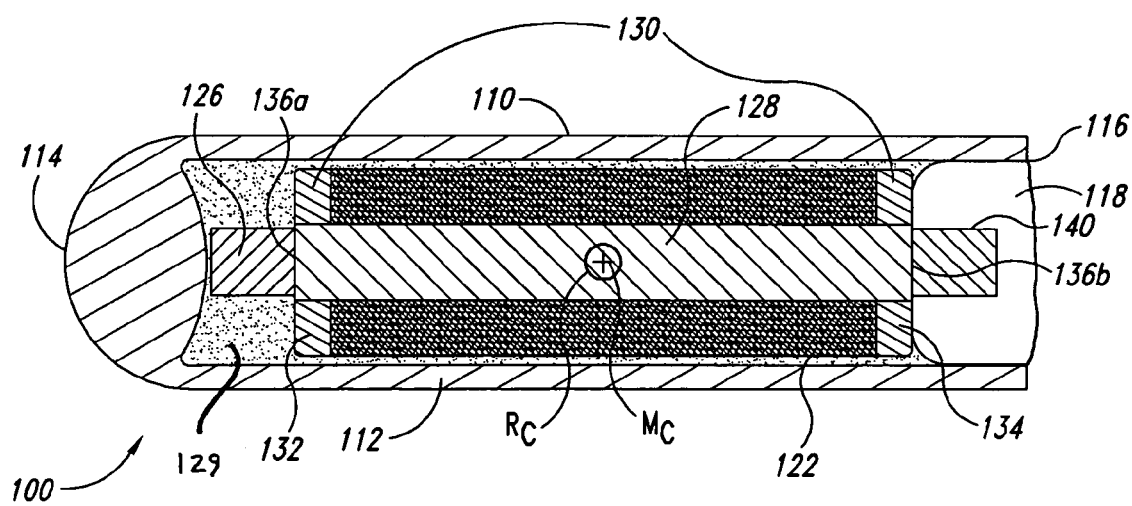
FIG. 1B is a cross-sectional view of the wireless marker of FIG. 1A taken along line 1B-1B.

FIG. 1B is a cross-sectional view of the marker 100 along line 1B-1B that illustrates an imaging element 130 in accordance with an embodiment of the invention. The imaging element 130 illustrated in FIGS. 1A-B includes a first contrast element 132 and second contrast element 134. The first and second contrast elements 132/134 are generally configured with respect to the magnetic transponder 120 so that the marker 100 has a radiographic centroid $R_c$ that is at least substantially coincident with the magnetic centroid $M_c$ of the magnetic transponder 120. For example, when the imaging element 130 includes two contrast elements, the contrast elements can be arranged symmetrically with respect to the magnetic transponder 120 and/or each other. The contrast elements can also be radiographically distinct from the magnetic transponder 120. In such an embodiment, the symmetrical arrangement of distinct contrast elements enhances the ability to accurately determine the radiographic centroid of the marker 100 in a radiographic image.

The first and second contrast elements 132/134 illustrated in FIGS. 1A-B are continuous rings positioned at opposing ends of the core 128. The first contrast element 132 can be at or around a first end 136a of the core 128, and the second contrast element 134 can be at or around a second end 136b of the core 128. The continuous rings shown in FIGS. 1A-B have substantially the same diameter and thickness. The first and second contrast elements 132/134, however, can have other configurations and/or be in other locations relative to the core 128 in other embodiments. For example, the first and second contrast elements 132/134 can be rings with different diameters and/or thicknesses.

The radiographic centroid of the image produced by the imaging element 130 does not need to be absolutely coincident with the magnetic centroid $M_c$, but rather the radiographic centroid and the magnetic centroid should be within an acceptable range. For example, the radiographic centroid $R_c$ can be considered to be at least approximately coincident with the magnetic centroid $M_c$ when the offset between the centroids is less than approximately 5 mm. In more stringent applications, the magnetic centroid $M_c$ and the radiographic centroid $R_c$ are considered to be at least substantially coincident with each other when the offset between the centroids is 2 mm or less. In other applications, the magnetic centroid $M_c$ is at least approximately coincident with the radiographic centroid $R_c$ when the centroids are spaced apart by a distance not greater than half the length of the magnetic transponder 120 and/or the marker 100.

The imaging element 130 can be made from a material and configured appropriately to absorb a high fraction of incident photons of a radiation beam used for producing the radiographic image. For example, when the imaging radiation has high acceleration voltages in the megavoltage range, the imaging element 130 is made from, at least in part, high density materials with sufficient thickness and cross-sectional area to absorb enough of the photon fluence incident on the imaging element to be visible in the resulting radiograph. Many high energy beams used for therapy have acceleration voltages of 6 MV-25 MV, and these beams are often used to produce radiographic images in the 5 MV-10 MV range, or more specifically in the 6 MV-8 MV range. As such, the imaging element 130 can be made from a material that is sufficiently absorbent of incident photon fluence to be visible in an image produced using an beam with an acceleration voltage of 5 MV-10 MV, or more specifically an acceleration voltage of 6 MV-8 MV.

Several specific embodiments of imaging elements 130 can be made from gold, tungsten, platinum and/or other high density metals. In these embodiments the imaging element 130 can be composed of materials having a density of 19.25 g/cm$^3$ (density of tungsten) and/or a density of approximately 21.4 g/cm$^3$ (density of platinum). Many embodiments of the imaging element 130 accordingly have a density not less than 19 g/cm$^3$. In other embodiments, however, the material(s) of the imaging element 130 can have a substantially lower density. For example, imaging elements with lower density materials are suitable for applications that use lower energy radiation to produce radiographic images. Moreover, the first and second contrast elements 132/134 can be composed of different materials such that the first contrast element 132 can be made from a first material and the second contrast element 134 can be made from a second material.

Referring to FIG. 1B, the marker 100 can further include a module 140 at an opposite end of the core 128 from the capacitor 126. In the embodiment of the marker 100 shown in FIG. 1B, the module 140 is configured to be symmetrical with respect to the capacitor 126 to enhance the symmetry of the radiographic image. As with the first and second contrast elements 132/134, the module 140 and the capacitor 126 are arranged such that the magnetic centroid of the marker is at least approximately coincident with the radiographic centroid of the marker 100. The module 140 can be another capacitor that is identical to the capacitor 126, or the module 140 can be an electrically inactive element. Suitable electrically inactive modules include ceramic blocks shaped like the capacitor 126 and located with respect to the coil 122, the core 128 and the imaging element 130 to be symmetrical with each other. In still other embodiments the module 140 can be a different type of electrically active element electrically coupled to the magnetic transponder 120.

One specific process of using the marker involves imaging the marker using a first modality and then tracking the target of the patient and/or the marker using a second modality. For example, the location of the marker relative to the target can be determined by imaging the marker and the target using radiation. The marker and/or the target can then be localized and tracked using the magnetic field generated by the marker in response to an excitation energy. Suitable applications for such bi-modal use of the marker 100 and suitable systems for localizing/tracking the marker are disclosed and described in the following pending U.S. application Nos., all of which are incorporated herein by reference: Ser. Nos. 10/438,550; 10/334,700; 09/877,498; 09/954,700; 10/213,980; 10/679,801; and 10/382,123.

Figure 1C:
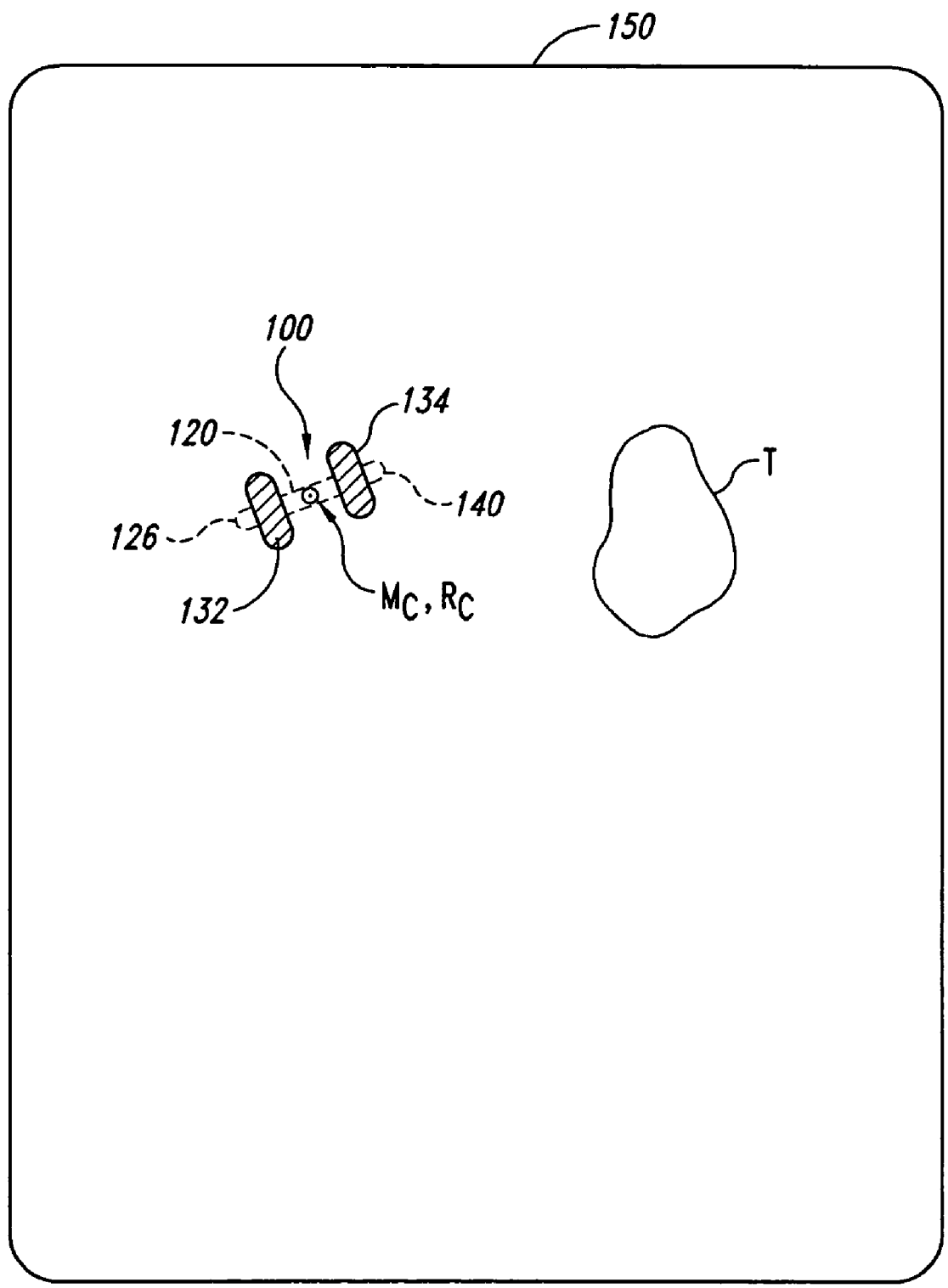
FIG. 1C is an illustration of a radiographic image of the marker of FIGS. 1A-B.

The marker 100 shown in FIGS. 1A-B is expected to provide an enhanced radiographic image compared to conventional magnetic markers for more accurately determining the relative position between the marker and the target of a patient. FIG. 1C, for example, illustrates a radiographic image 150 of the marker 100 and a target T of the patient. The first and second contrast elements 132/134 are expected to be more distinct in the radiographic image 150 because they can be composed of higher density materials than the components of the magnetic transponder 120. The first and second contrast elements 132/134 can accordingly appear as bulbous ends of a dumb-bell shape in applications in which the components of the magnetic transponder 120 are visible in the image. In certain megavolt applications, the components of the magnetic transponder 120 may not appear at all on the radiographic image 150 such that the first and second contrast elements 132/134 will appear as distinct regions that are separate from each other. In either embodiment, the first and second contrast elements 132/134 provide a reference frame in which the radiographic centroid $R_c$ of the marker 100 can be located in the image 150. Moreover, because the imaging element 130 is configured so that the radiographic centroid $R_c$ is at least approximately coincident with the magnetic centroid $M_c$, the relative offset or position between the target T and the magnetic centroid $M_c$ can be accurately determined using the marker 100. The embodiment of the marker 100 illustrated in FIGS. 1A-C, therefore, is expected to mitigate errors caused by incorrectly estimating the radiographic and magnetic centroids of markers in radiographic images.

Figure 2A:
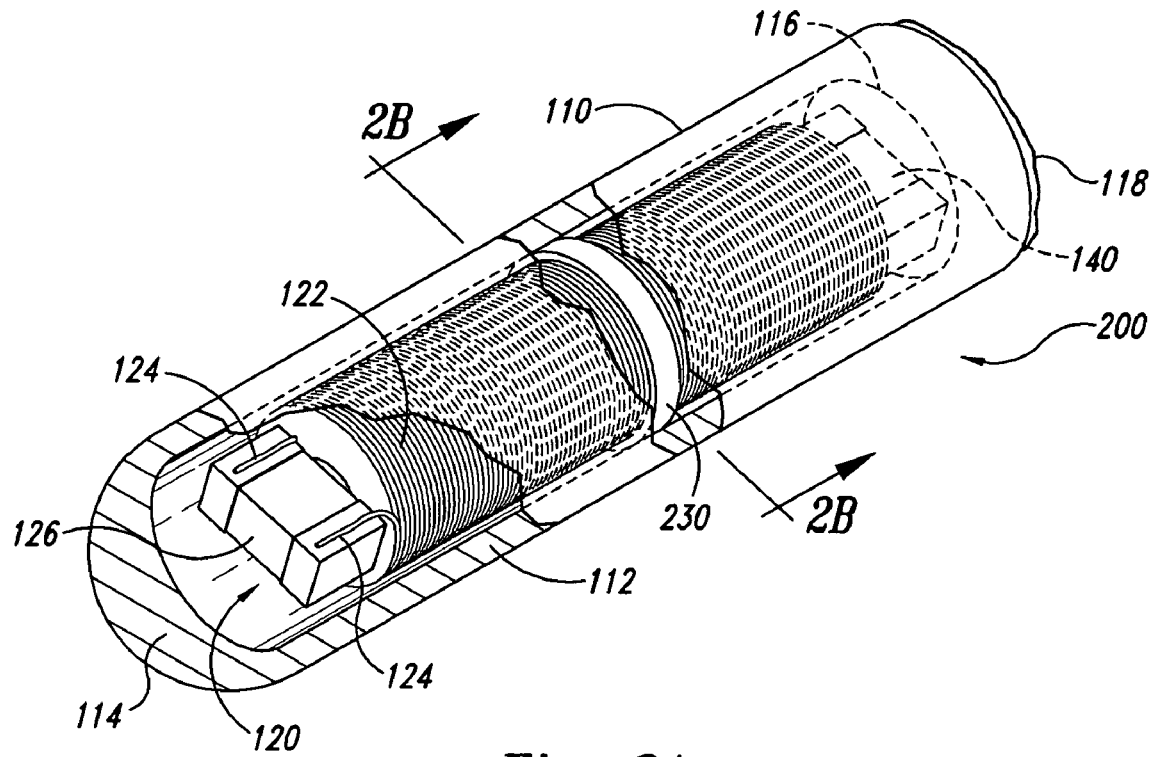
FIG. 2A is an isometric view of a wireless marker in accordance with another embodiment of the invention.
Figure 2B:
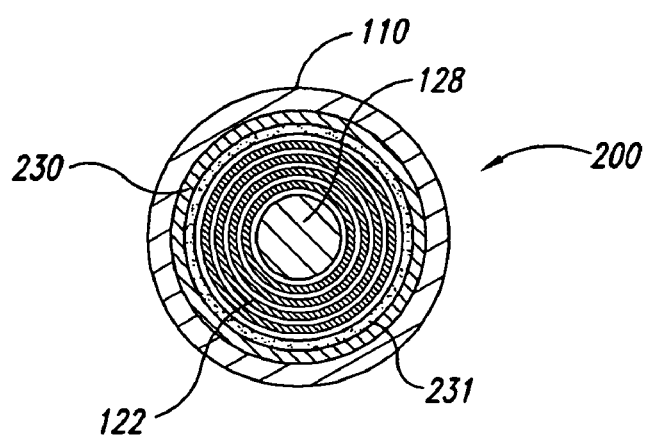
FIG. 2B is a cross-sectional view of the wireless marker of FIG. 2A taken along line 2B-2B.

FIG. 2A is an isometric view of a marker 200 with a cut away portion to illustrate internal components, and FIG. 2B is a cross-sectional view of the marker 200 taken along line 2B-2B of FIG. 2A. The marker 200 is similar to the marker 100 shown above in FIG. 1A, and thus like reference numbers refer to like components. The marker 200 differs from the marker 100 in that the marker 200 includes an imaging element 230 defined by a single contrast element. The imaging element 230 is generally configured relative to the magnetic transponder 120 so that the radiographic centroid of the marker 200 is at least approximately coincident with the magnetic centroid of the magnetic transponder 120. The imaging element 230, more specifically, is a ring extending around the coil 122 at a medial region of the magnetic transponder 120. The imaging element 230 can be composed of the same materials described above with respect to the imaging element 130 in FIGS. 1A-B. The imaging element 230 can have an inner diameter that is approximately equal to the outer diameter of the coil 122, and an outer diameter within the casing 110. As shown in FIG. 2B, however, a spacer 231 can be between the inner diameter of the imaging element 230 and the outer diameter of the coil 122.

The marker 200 is expected to operate in a manner similar to the marker 100 described above. The marker 200, however, does not have two separate contrast elements that provide two distinct, separate points in a radiographic image. The imaging element 230 is still highly useful in that it identifies the radiographic centroid of the marker 200 in a radiographic image, and it can be configured so that the radiographic centroid of the marker 200 is at least approximately coincident with the magnetic centroid of the magnetic transponder 120.

Figure 3A:
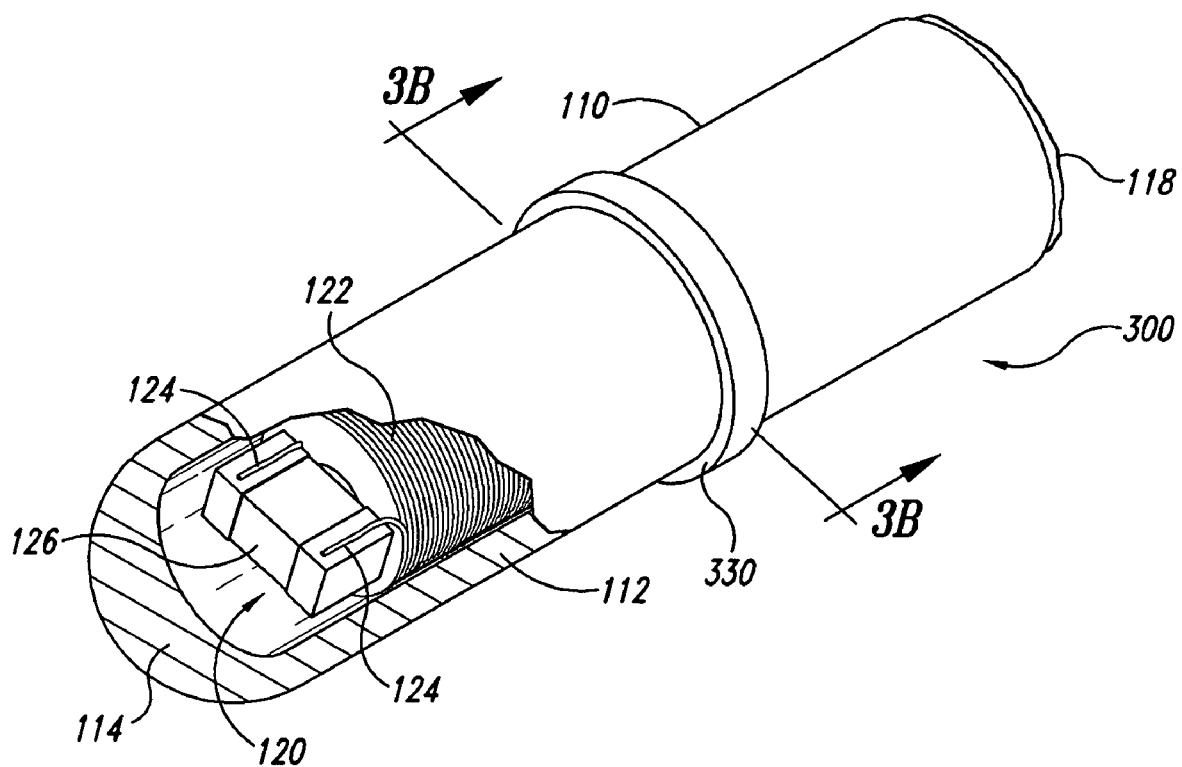
FIG. 3A is an isometric view of a wireless marker in accordance with another embodiment of the invention.
Figure 3B:
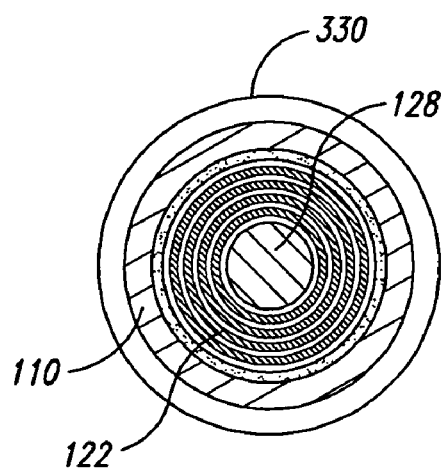
FIG. 3B is a cross-sectional view of the wireless marker of FIG. 3A taken along line 3B-3B.

FIG. 3A is an isometric view of a marker 300 having a cut away portion, and FIG. 3B is a cross-sectional view of the marker 300 taken along line 3B-3B. The marker 300 is substantially similar to the marker 200 shown in FIGS. 2A-B, and thus like reference numbers refer to like components in FIGS. 1A-3B. The imaging element 330 can be a high density ring configured relative to the magnetic transponder 120 so that the radiographic centroid of the marker 300 is at least approximately coincident with the magnetic centroid of the magnetic transponder 120. The marker 300, more specifically, includes an imaging element 330 around the casing 110. The marker 300 is expected to operate in much the same manner as the marker 200 shown in FIGS. 2A-B.

Figure 4:
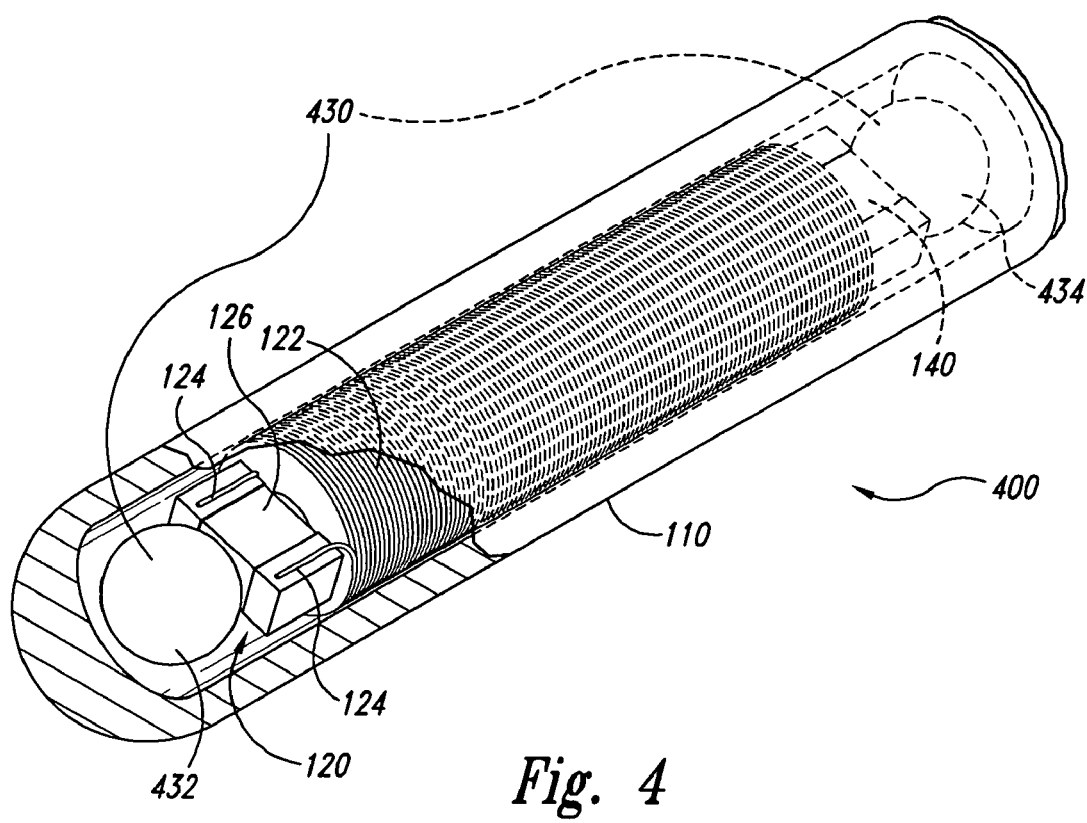
FIG. 4 is an isometric view of a wireless marker in accordance with yet another embodiment of the invention with a section cut away to illustrate internal components.

FIG. 4 is an isometric view with a cut away portion illustrating a marker 400 in accordance with another embodiment of the invention. The marker 400 is similar to the marker 100 shown in FIGS. 1A-C, and thus like reference numbers refer to like components in these Figures. The marker 400 has an imaging element 430 including a first contrast element 432 at one end of the magnetic transponder 120 and a second contrast element 434 at another end of the magnetic transponder 120. The first and second contrast elements 432/434 are spheres composed of suitable high density materials. The contrast elements 432/434, for example, can be composed of gold, tungsten, platinum or other suitable high-density materials for use in radiographic imaging. The marker 400 is expected to operate in a manner similar to the marker 100, as described above.

Figure 5:
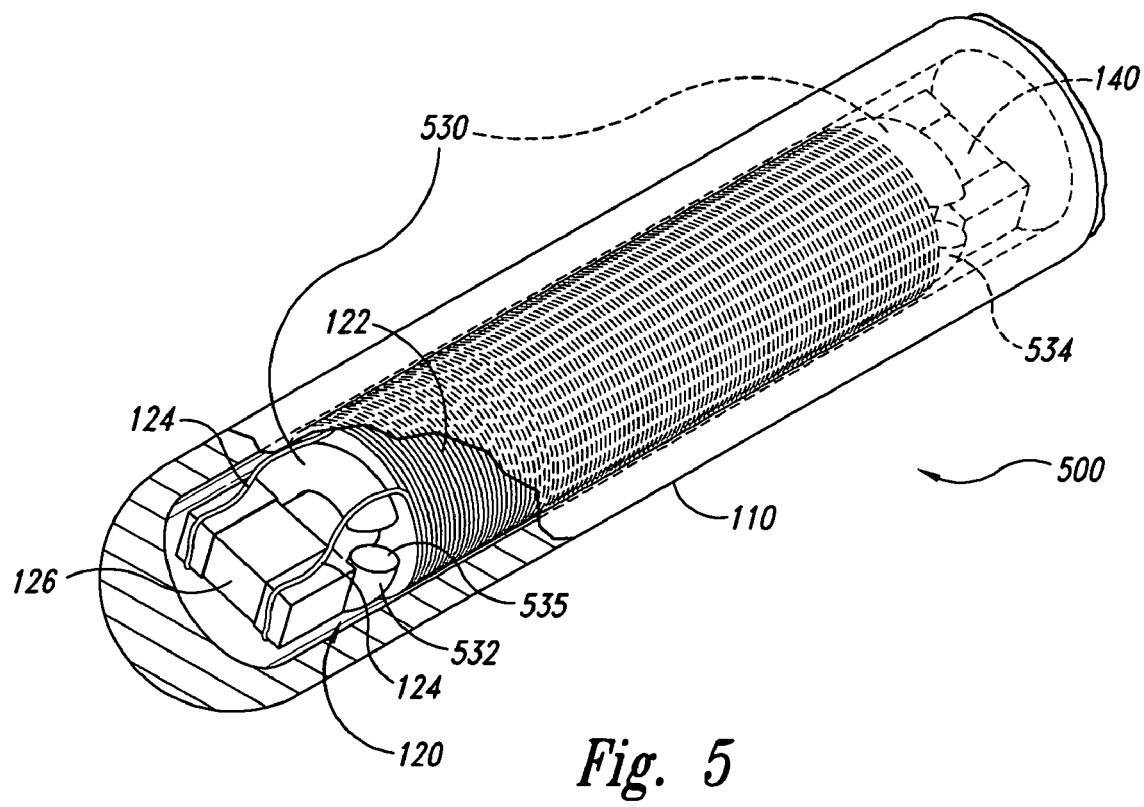
FIG. 5 is an isometric view of a wireless marker in accordance with still another embodiment of the invention with a section cut away to illustrate internal components.

FIG. 5 is an isometric view with a cut away portion of a marker 500 in accordance with yet another embodiment of the invention. The marker 500 is substantially similar to the markers 100 and 400 shown in FIGS. 1A-C and FIG. 4, and thus like reference numbers refer to like components in these Figures. The marker 500 includes an imaging element 530 including a first contrast element 532 and a second contrast element 534. The first and second contrast elements 532/534 can be positioned proximate to opposing ends of the magnetic transponder 120. The first and second contrast elements 532/534 can be discontinuous rings having a gap 535 to mitigate eddy currents. The contrast elements 532/534 can be composed of the same materials as described above with respect to the contrast elements of other imaging elements in accordance with other embodiments of the invention.

Additional embodiments of markers in accordance with the invention can include imaging elements incorporated into or otherwise integrated with the casing 110, the core 128 (FIG. 1B) of the magnetic transponder 120, and/or the adhesive 129 (FIG. 1B) in the casing. For example, particles of a high density material can be mixed with ferrite and extruded to form the core 128. Alternative embodiments can mix particles of a high density material with glass or another material to form the casing 110, or coat the casing 110 with a high-density material. In still other embodiments, a high density material can be mixed with the adhesive 129 and injected into the casing 110. Any of these embodiments can incorporate the high density material into a combination of the casing 110, the core 128 and/or the adhesive 129. Suitable high density materials can include tungsten, gold and/or platinum as described above.

From the foregoing, it will be appreciated that specific embodiments of the invention have been described herein for purpose of illustration, but that various modifications may be made without deviating from the spirit and scope of the invention. For example, the imaging elements can be composed of more than one material, or the imaging elements of the various embodiments can be interchanged or combined with each other. Another embodiment could accordingly have a ring-like contrast element at the other end of the transponder. Accordingly, the invention is not limited except as by the appended claims.

We claim:

1. A wireless marker for localizing a target of a patient, comprising:

a casing;

a magnetic transponder at least partially encased in the casing, the magnetic transponder configured to produce a wirelessly transmitted magnetic field having a magnetic centroid within the casing in response to a wirelessly transmitted excitation energy; and an imaging element carried by the casing and/or the magnetic transponder, the imaging element having a radiographic profile in a radiographic image such that the marker has a radiographic centroid at least approximately coincident with the magnetic centroid.

2. The marker of claim 1 wherein the magnetic transponder comprises a ferrite core, a plurality of windings around the core, and a capacitor electrically coupled to the windings.

3. The marker of claim 1 wherein:
the magnetic transponder has a first end and a second end; and
the imaging element comprises a first contrast element and a second contrast element, the first and second contrast elements being configured symmetrically with respect to the magnetic transponder.

4. The marker of claim 1 wherein:
the magnetic transponder has a first end and a second end; and
the imaging element comprises a first contrast element at the first end of the magnetic transponder and a second contrast element at the second end of the magnetic transponder.

5. The marker of claim 4 wherein the first contrast element comprises a first ring and the second contrast element comprises a second ring.

6. The marker of claim 5 wherein the first and second rings are continuous.

7. The marker of claim 5 wherein the first and second rings are discontinuous annular members having a gap.

8. The marker of claim 4 wherein the first contrast element is a first sphere and the second contrast element is a second sphere.

9. The marker of claim 4 wherein the first and second contrast elements comprise Au, W and/or Pt.

10. The marker of claim 1 wherein the imaging element has a density of at least approximately 19 g/cm$^3$.

11. The marker of claim 1 wherein the imaging element is sufficiently absorbent of incident photon fluence of a megavolt photon therapy beam to be visible in a radiographic image generated using such a therapy beam.

12. The marker of claim 1 wherein the imaging element is a ring around a medial region of the magnetic transponder.

13. The marker of claim 12 wherein the ring is within the casing.

14. The marker of claim 12 wherein the ring is exterior of the casing.

15. The marker of claim 1 wherein:
the magnetic transponder comprises a ferrite core having a first end and a second end, a plurality of windings around the core, and a capacitor electrically coupled to the windings and located at the first end of the core, wherein the capacitor has a radiographic profile in a radiographic image; and
the marker further comprises a module at the second end of the core, the module having a radiographic profile similar to the radiographic profile of the capacitor.

16. The marker of claim 15 wherein the capacitor and the module are arranged to be approximately symmetrical with respect to the core and the windings.

17. The marker of claim 15 wherein:
the capacitor and the module are arranged to be approximately symmetrical with respect to the core and the windings; and
the imaging element comprises a first contrast element at least proximate to the first end of the core and a second contrast element at least proximate to the second end of the core.

18. The marker of claim 17 wherein the first contrast element comprises a first ring around the first end of the core and the second contrast element comprises a second ring around the second end of the core.

19. The marker of claim 17 wherein the first contrast element comprises a first sphere at least proximate to the first end of the core and the second contrast element comprises a second sphere at least proximate to the second end of the core.

20. A wireless marker for localizing a target of a patient, comprising:
a casing;
a magnetic transponder in the casing, the magnetic transponder has a magnetic centroid within the casing, the magnetic transponder configured to produce a wirelessly transmitted magnetic field in response to a wirelessly transmitted excitation field, and the magnetic transponder having a first density; and
an imaging element carried by the casing and/or the magnetic transponder, the imaging element having a second density greater than the first density of the magnetic transponder; wherein
the imaging element has a radiographic profile in a radiographic image such that the marker has a radiographic centroid at least approximately coincident with the magnetic centroid.

21. The marker of claim 20 wherein:
the magnetic transponder has a first end and a second end; and
the imaging element comprises a first contrast element and a second contrast element, the first and second contrast elements being configured symmetrically with respect to the magnetic transponder.

22. The marker of claim 20 wherein:
the magnetic transponder has a first end and a second end; and
the imaging element comprises a first contrast element at the first end of the magnetic transponder and a second contrast element at the second end of the magnetic transponder.

23. The marker of claim 20 wherein the first density is less than 19 g/cm$^3$ and the second density is not less than 19 g/cm$^3$.

24. A wireless marker for localizing a target of a patient, comprising:
a casing;
a magnetic transponder at least partially encased in the casing, the magnetic transponder has a magnetic centroid within the casing, the magnetic transponder configured to produce a wirelessly transmitted magnetic field in response to a wirelessly transmitted excitation field; and
an imaging element carried by the casing and/or the magnetic transponder, the imaging element being sufficiently absorbent of incident photon fluence of a megavolt photon therapy beam to be visible in a radiographic image generated using such a therapy beam; wherein
the imaging element has a radiographic profile in a radiographic image such that the marker has a radiographic centroid at least approximately coincident with the magnetic centroid.

25. The marker of claim 24 wherein:
the magnetic transponder has a first end and a second end; and
the imaging element comprises a first contrast element and a second contrast element, the first and second contrast elements being configured symmetrically with respect to the magnetic transponder.

26. The marker of claim 24 wherein:
the magnetic transponder has a first end and a second end; and
the imaging element comprises a first contrast element at the first end of the magnetic transponder and a second contrast element at the second end of the magnetic transponder.

27. The marker of claim 24 wherein the magnetic transponder has a first density less than 19 g/cm$^3$ and the imaging element has a second density not less than 19 g/cm$^3$.

28. A wireless marker for localizing a target of a patient, comprising:
a casing;
a magnetic transponder at least partially encased in the casing, the magnetic transponder has a magnetic centroid within the casing, the magnetic transponder configured to produce a wirelessly transmitted magnetic field in response to a wirelessly transmitted excitation field; and
an imaging element carried by the casing and/or the magnetic transponder, the imaging element having a density of at least 19 g/cm$^3$; wherein
the imaging element has a radiographic profile in a radiographic image such that the marker has a radiographic centroid at least approximately coincident with the magnetic centroid.

29. The marker of claim 28 wherein:
the magnetic transponder has a first end and a second end; and
the imaging element comprises a first contrast element and a second contrast element, the first and second contrast elements being configured symmetrically with respect to the magnetic transponder.

30. The marker of claim 28 wherein:
the magnetic transponder has a first end and a second end; and
the imaging element comprises a first contrast element at the first end of the magnetic transponder and a second contrast element at the second end of the magnetic transponder.

31. A wireless marker for localizing a target of a patient, comprising:
a casing;
a magnetic transponder at least partially encased in the casing, the magnetic transponder configured to produce a wirelessly transmitted magnetic field having a magnetic centroid within the casing in response to a wirelessly transmitted excitation field; and
an imaging element incorporated with the casing and/or the magnetic transponder, the imaging element producing a radiographic profile in a radiographic image such that the marker has a radiographic centroid at least approximately coincident with the magnetic centroid.

32. The marker of claim 31 wherein:
the magnetic transponder has a first end and a second end; and
the imaging element comprises a first contrast element and a second contrast element, the first and second contrast elements being configured symmetrically with respect to the magnetic transponder.

33. The marker of claim 31 wherein:
the magnetic transponder has a first end and a second end; and
the imaging element comprises a first contrast element at the first end of the magnetic transponder and a second contrast element at the second end of the magnetic transponder.

34. The marker of claim 31 wherein the magnetic transponder comprises a ferrite core, a plurality of windings around the core, and a capacitor electrically coupled to the windings.

35. The wireless marker of claim 34 wherein the imaging element comprises a high density material integrated into the ferrite core.

36. The wireless marker of claim 31 wherein the imaging element comprises a material having a density greater than or equal to 19 g/cm$^3$ integrated into the casing.

37. The wireless marker of claim 31 wherein the casing is sealed by a sealant and the imaging element comprises a material having a density greater than or equal to 19 g/cm$^3$ integrated with an adhesive in the casing.

* * * * *